United States Patent
Norman

(10) Patent No.: US 10,267,717 B2
(45) Date of Patent: *Apr. 23, 2019

(54) ABRASION WEAR TESTER

(71) Applicant: Scott H Norman, LaGrange, KY (US)

(72) Inventor: Scott H Norman, LaGrange, KY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/999,503

(22) Filed: May 16, 2016

(65) Prior Publication Data

US 2016/0377519 A1 Dec. 29, 2016

Related U.S. Application Data

(63) Continuation-in-part of application No. 13/986,695, filed on May 24, 2013, now Pat. No. 9,341,555.

(60) Provisional application No. 61/688,929, filed on May 24, 2012.

(51) Int. Cl.
*G01N 3/56* (2006.01)
*G01N 3/02* (2006.01)
*G01N 3/08* (2006.01)

(52) U.S. Cl.
CPC .............. *G01N 3/56* (2013.01); *G01N 3/02* (2013.01)

(58) Field of Classification Search
CPC ............ G01N 3/56; G01N 3/567; G01N 3/08; G01N 3/02
USPC .......... 73/7, 1.89, 9, 150 R, 818; 204/192.16
See application file for complete search history.

(56) References Cited

U.S. PATENT DOCUMENTS

| | | |
|---|---|---|
| 2,329,062 A | 9/1943 | Leape |
| 2,734,375 A | 2/1956 | Galbraith et al. |
| 3,359,783 A | 12/1967 | Scheiman |
| 3,835,697 A | 9/1974 | Schneider |
| 3,919,719 A | 11/1975 | Wright |
| 4,462,245 A | 7/1984 | Gould et al. |
| 4,936,135 A | 6/1990 | Annis |
| 5,533,382 A | 7/1996 | Clerkin |
| 5,542,281 A | 8/1996 | Lee et al. |
| 5,557,039 A | 9/1996 | Annis et al. |
| 5,795,989 A | 8/1998 | Simmons et al. |
| 5,804,706 A | 9/1998 | Williston |
| 5,835,621 A | 11/1998 | Vandermeerssche |
| 6,000,284 A | 12/1999 | Shin et al. |

(Continued)

*Primary Examiner* — Lisa M Caputo
*Assistant Examiner* — Suman K Nath
(74) *Attorney, Agent, or Firm* — Carrithers Law Office, PLLC

(57) ABSTRACT

An apparatus for measuring the anti-wear nature of a surface of given article to test the article or coating thereon for wear and abrasion resistance. A selected abrasive paper strip or tape is pulled under controlled tension from a first feed reel which can control tension on the strip onto another second reel controlled at a selected speed and torque. The test part apparatus is capable of repetitive cycles. For example, a test cycle process may include the steps of pushing a finger probe against the moving selected abrasive paper in contact with a the test sample surface having a selected surface area, holding the finger probe against the paper which between the finger probe and surface of the article for a selected time and distance, and removing the finger probe pressure from the paper and the test article surface. The number of cycles required to wear through the coating on the sample is recorded and compared to other test samples. In one embodiment, the abrasive paper strip is moistened by being pulled through a selected liquid contained in a vessel located just before the paper strip abrades the sample.

3 Claims, 8 Drawing Sheets

(56) References Cited

U.S. PATENT DOCUMENTS

| | | |
|---|---|---|
| 6,026,680 A | 2/2000 | Mann |
| 6,247,356 B1 | 6/2001 | Merck et al. |
| 6,467,330 B1 | 10/2002 | Vizintin et al. |
| 6,477,895 B2 | 11/2002 | Lawson et al. |
| 6,612,150 B2 | 9/2003 | Srinivasan |
| 7,013,705 B2 | 3/2006 | Wortmann et al. |
| 7,448,941 B2 | 11/2008 | Drew |
| 7,966,866 B2 | 6/2011 | Hansma et al. |
| 2002/0129637 A1 | 9/2002 | Lawson et al. |
| 2002/0194894 A1 | 12/2002 | Srinivasan |
| 2004/0099059 A1 | 5/2004 | Tarumi |
| 2005/0050942 A1 | 3/2005 | Schmitt |
| 2005/0120774 A1 | 6/2005 | Shinohara et al. |
| 2008/0000285 A1 | 1/2008 | Gregory et al. |
| 2009/0078035 A1 | 3/2009 | Mecca et al. |

ABRASION WEAR TESTER

CROSS REFERENCE TO RELATED APPLICATIONS

This application is a Continuation-In-Part of U.S. Pat. No. 9,341,555 which issued on May 17, 2016 from U.S. application Ser. No. 13/986,695 filed on May 24, 2013 claiming priority from U.S. Provisional Application Ser. No. 61/688,929 filed on May 24, 2012 which is incorporated by reference herein.

TECHNICAL FIELD

The present invention relates to devices which test the surface of a given test sample for resistance to wear.

BACKGROUND OF THE INVENTION

Many items of manufacture are sold based on function as well as looks. These items are often provided with a protective or ornamental coating which can wear off with extended use. For example, the alphanumeric and special function keys on a cell phone, computer keyboard, radio, television, TV remote, game console, appliances and the like, are used repeatedly. Membrane switches and keypads and silicon rubber keypads are commonly present on such devices. The switches and keys are subject to repeated actuations, typically by a human finger. Oils and salts in human skin helps to break down or wear away identifying symbols made from paints, inks or coatings on the surface of keys or switches. Keys and switches are also subject to other conditions which cause wear to the exposed surfaces such as wiping, cleaning, and rubbing during normal use, handling, shipping, and storage.

After repeated use, the symbols or graphics on the appliance keys wear away to the point that symbols are unattractive or totally illegible, possibly rendering the items unusable. For example, it is important to determine the resistance to wear of buttons or number pads of items such as video or tv remotes which may wear off after continued use. The infrequent user who is not as familiar the function of all the keys can become very frustrated when trying to use such a device with often used keys which are now unlabeled.

Manufacturers employ tests of various types such ensure quality and reliability of alphanumeric and symbolic labels on keys and switches. Examples of such tests include a test wherein a sharp pinpoint is used to scratch a surface of a test sample. The amount of damage is measured and compared to other tested samples. Another type of test uses a spinning ball which is moistened with a polishing slurry which is urged against the test surface for a selected amount of time. The resulting amount of wear is measured and compared to other test samples.

Examples of surfaces types to be tested include items with coatings such as paints, acrylics and the like, items with applied or adhesive layers such as plastics and Mylar, and injection molded items wherein alphanumeric symbols are molded within the key in a process called double shot injection molding. Due to the use of extremely thin overlays and new types of coatings which contain the symbols which are applied to the surface of keys or other surfaces on appliances, toys, computers, and so forth, the quality, reliability and durability of these applied symbols is critical.

DESCRIPTION OF THE RELATED ART

U.S. Pat. No. 5,533,382 for ABRASION TESTER by Clerkin issued on Jul. 8, 1996 teaches a device wherein an abrasive strip is pulled from one reel onto another reel at a given speed and tension. A counter roller urges the moving abrasive strip against the surface of an insulated wire test sample for a given amount of time. Another device measures the dielectric constant (insulative property) of the insulation to determine the outcome of the abrasion test. Clerkin does not measure the physical depth of wear to the insulation, does not provide a means of applying a liquid to the abrasive wire, and does not provide a programmable cycle controller, as are provided in the present invention.

U.S. Pat. No. 7,013,705 for METHOD AND DEVICE FOR DETERMINATION OF THE WEAR RESISTANCE OF A SURFACE by Wortmann et al. issued on Mar. 21, 2006 teaches a device wherein an abrasive belt is pulled from one reel onto another reel at a given speed and tension. A counter-body urges the abrasive belt against the surface of a test sample with a selected force for a given amount of time. The amount of wear is measured by the distance which the counter-body moved into the test sample as the test was done. Wortmann provides no means of adjusting the force applied to the sample by the counter-body, does not provide a device wherein a user may program an automatic test cycle into the device, as is provided by the present invention. Further, Wortmann is silent with respect to simulating the actual stroke of a human finger on a surface and with respect to a means of applying a liquid to the belt.

FIGS. 10 and 11 show Applicant's prior art embodiment of Applicant's abrader instrument from 1986.

SUMMARY OF THE INVENTION

The present invention utilizes an abrasive material applied to at least one side of a film, ribbon or strip of paper or polymer film or the abrasive material may be incorporated within a composite material of paper, plastic or combination thereof. The following description may utilize the term "paper" as for example "paper strip"; however, the connotation is applicable to a plastic or composite film or ribbon as well.

In accordance with the present invention, there is provided an abrasive tester for testing the wear resistance of the surface of a selected test sample comprising a horizontal base member and a frame defining a vertical back wall connected perpendicular to the base member. The back wall includes a paper supply reel rotatably connected to a brake means which is rigidly connected to the back wall. The paper supply reel has a continuous strip of abrasive material paper wrapped there around. The strip or ribbon or film of paper is selected from abusive stock having a particular density, amount of stretch, thickness, width, and composition An abrasive may be applied to one side of the strip or ribbon or comprise a composite material having an abrasive material throughout. Moreover, a synthetic paper having selected properties may also be selected for the test. The ribbon may run dry or be capable of being pre-treated with a selected liquid and then being capable of abrading a given test sample using the abrasive tester.

One preferred embodiment includes a wear unit includes a peg arm assembly slidably connected to the back wall of the unit which includes a first set of three friction pegs. The friction pegs are capable of providing tension to the ribbon/strip as the abrasive strip is pulled through the first set of three friction pegs. A liquid holding tank containing a selected liquid is positioned to receive the peg arm and the first set of friction pegs when the peg arm is lowered into the liquid contained in the liquid tank. A paper guide assembly is slidably connected to the back wall and includes two paper guide rollers and a second set of three friction pegs. The two paper guide rollers are rotatably connected to the paper guide assembly. The second set of three friction pegs are rigidly connected to the paper guide assembly. The paper guide assembly also includes a finger probe connected to a piston extending from a first pneumatic cylinder which is attached to the paper guide assembly and is capable of extending the finger probe against the paper and thereby urging the paper against a test sample. A second pneumatic cylinder is capable of moving the paper guide assembly to and from a start position. First and second air solenoids are capable of activating the first and the second pneumatic cylinders, respectively. A first air pressure regulator supplies regulated air to the first solenoid at a selected pressure which is appropriate to urge the finger probe against the paper and the test sample at a selected force. A second air pressure regulator is capable of supplying regulated air to the second solenoid at a selected pressure required to slide the paper guide assembly to and from the start position. A paper drive roller assembly includes a paper drive roller and a paper pressure roller which is rotatably connected to the paper drive roller assembly. A paper drive motor is capable of driving the paper drive roller. The pressure roller presses the paper against the paper drive roller so that the paper drive roller grips and drives the paper. The drive roller is capable of pulling the paper from the paper supply reel, through the first set of friction pegs on the friction peg assembly, over the two guide rollers, against a hemispherical end of the finger probe and through the second set of friction pegs on the paper guide assembly. A paper rewind reel is rotatably connected to the back wall and is driven by a rewind motor through a slip clutch. The rewind reel is capable of rewinding the paper coming off of the paper drive roller. A controller controls the first and the second solenoids, the paper roller drive motor and the rewind motor. The controller is capable of being programmed for tests comprising multiple test cycles. The controller is capable of providing automatic and manual control of the paper drive motor and the first and the second solenoids. The automatic control is capable of simulating normal human operation of keys by providing a wiping action of the finger probe and the moving paper against the test sample. An operator display panel is capable of providing communication between an operator and the controller and allowing setup and operation of the wear tester.

The present invention provides a test which simulates the stroke of a human finger across the surface of a test sample. A continuous strip of paper is being pulled from one reel to another over a series of guide rollers and pegs. The paper moves just above the surface of the test sample and is periodically pressed down against the test sample by a 'finger probe". An example of a test sample is a key of a computer keyboard or a television remote control with a symbol being present on the surface of the key. The paper is moving at a rate of 1.5 to 2 inches per second. A 'finger probe' with an elastomeric approximately hemispherical tip is urged down against the moving paper and pushes the paper down against the surface of the test sample. At the same time that the moving paper comes into contact with the test sample, the finger probe is moved in the same direction and speed as the paper for a selected distance and time, after which the finger is raised off of the paper and returned to the original position. These three movements of the finger consisting of:

1. moving down against the paper
2. moving along with the paper
3. raising up off the paper and returning home constitute one test cycle. The user enters the number of cycles to be run at a touch sensitive operator's display.

An electronic controller is in control of the actions of the finger and paper. The time when that the finger is moved down to the paper, the length of time the fingers moves along with the paper and the time at which the finger is raised and returns home are all determined by timers in the program present in the electronic controller and are adjustable. The number of test cycles to be performed is adjustable as well. The controller also starts and stops the movement of the paper. All of these timers and the number of cycles to be run are adjustable at the operator's display. The Start and Stop keys are at the display as well.

Further, the paper may be pre-treated with a liquid such as lotions, oils or a solution that may contain simulated sweat or other liquids which simulate liquids present on an actual human finger. A synthetic paper which will not break down or tear easily when pre-treated with liquid is used.

In summary, the instant abrasive tester for testing the wear resistance of the surface of a selected test sample comprises or consists of a horizontal base member and a vertical back wall connected perpendicular to the base member. The back wall includes a supply reel rotatably connected to a brake means. The brake means is rigidly connected to the back wall. The supply reel has a continuous strip of abrasive material such as abrasive paper wrapped there around. The abrasive ribbon or strip is selected from the group consisting of a paper strip, a synthetic strip, and a combination paper and synthetic strip capable of being pre-treated with a selected liquid. The abrasive material on the strip is capable of abrading a given test sample using the abrasive tester. A peg arm is slidably connected to the back wall. The peg arm includes a first set of three friction studs or pegs connected to the peg arm. The friction pegs are capable of providing tension to the strip as the strip is pulled through the first set of three friction pegs. A liquid holding tank contains a selected liquid and is positioned to receive the peg arm and the first set of friction pegs when the peg arm is lowered into the liquid contained in the liquid tank. A guide assembly is slidably connected to the back wall. The guide assembly includes at least one and preferably two or more guide rollers and a second set of three friction pegs. The guide rollers are rotatably connected to the guide assembly. The second set of three friction pegs are rigidly connected to the guide assembly. The guide assembly includes a finger probe connected to a piston assembly extending from a first pneumatic finger probe cylinder. The first pneumatic finger probe cylinder is attached to the guide assembly and capable of extending the finger probe against the strip and thereby urging the strip against a test sample. A second pneumatic slide cylinder moves the guide assembly to and from a start position. A first air solenoid in fluid connection therewith activates the first pneumatic finger probe cylinder and a second air solenoid activates the second pneumatic slide cylinder. A first air pressure regulator supplies air at a regulated pressure to the first air solenoid at a selected pressure which is appropriate to urge the finger probe against the strip and the test sample at a selected force. A second air pressure regulator capable of supplying air at a regulated pressure to the second air solenoid at a selected pressure slides the guide assembly to and from the start position. A drive roller assembly includes a drive roller and a pressure roller being rotatably connected to the drive roller assembly. A drive motor is capable of driving the drive roller. The pressure roller presses the strip against the drive roller pulling the strip from the strip supply reel through the first set of friction pegs on the friction peg assembly, and over the two guide rollers and against a hemispherical end of the finger probe and through the second set of friction pegs on the guide assembly. A rewind reel is rotatably connected to the back wall. A rewind motor drives the rewind reel through a slip clutch. The rewind reel is capable of rewinding the strip coming off of the drive roller. A controller controlling the first air solenoid and the second air solenoid, the roller drive motor and the rewind motor, the controller capable of being programmed for tests comprising multiple test cycles, the controller capable of providing automatic control of the drive motor, the rewind motor and the first air solenoid and the second air solenoid thereby simulating normal human operation of keys by providing a wiping action of the finger probe and the moving strip against the test sample. The controller is capable of providing manual control of individual ones of the drive motor, the rewind motor, the first air solenoid, and the second air solenoid. An operator display panel provides communication between an operator and the controller and allows setup and operation of the wear tester.

It is an object of this invention to provide an abrasive wear tester including a counter-body which urges the abrasive medium against the test surface and wherein the force with which the counter-body is urged against that abrasive medium is selected by a control unit.

Other objects, features, and advantages of the invention will be apparent with the following detailed description taken in conjunction with the accompanying drawings showing a preferred embodiment of the invention.

BRIEF DESCRIPTION OF THE DRAWINGS

A better understanding of the present invention will be had upon reference to the following description in conjunction with the accompanying drawings in which like numerals refer to like parts throughout the views wherein.

DESCRIPTION OF THE PREFERRED EMBODIMENTS

Figure 1:
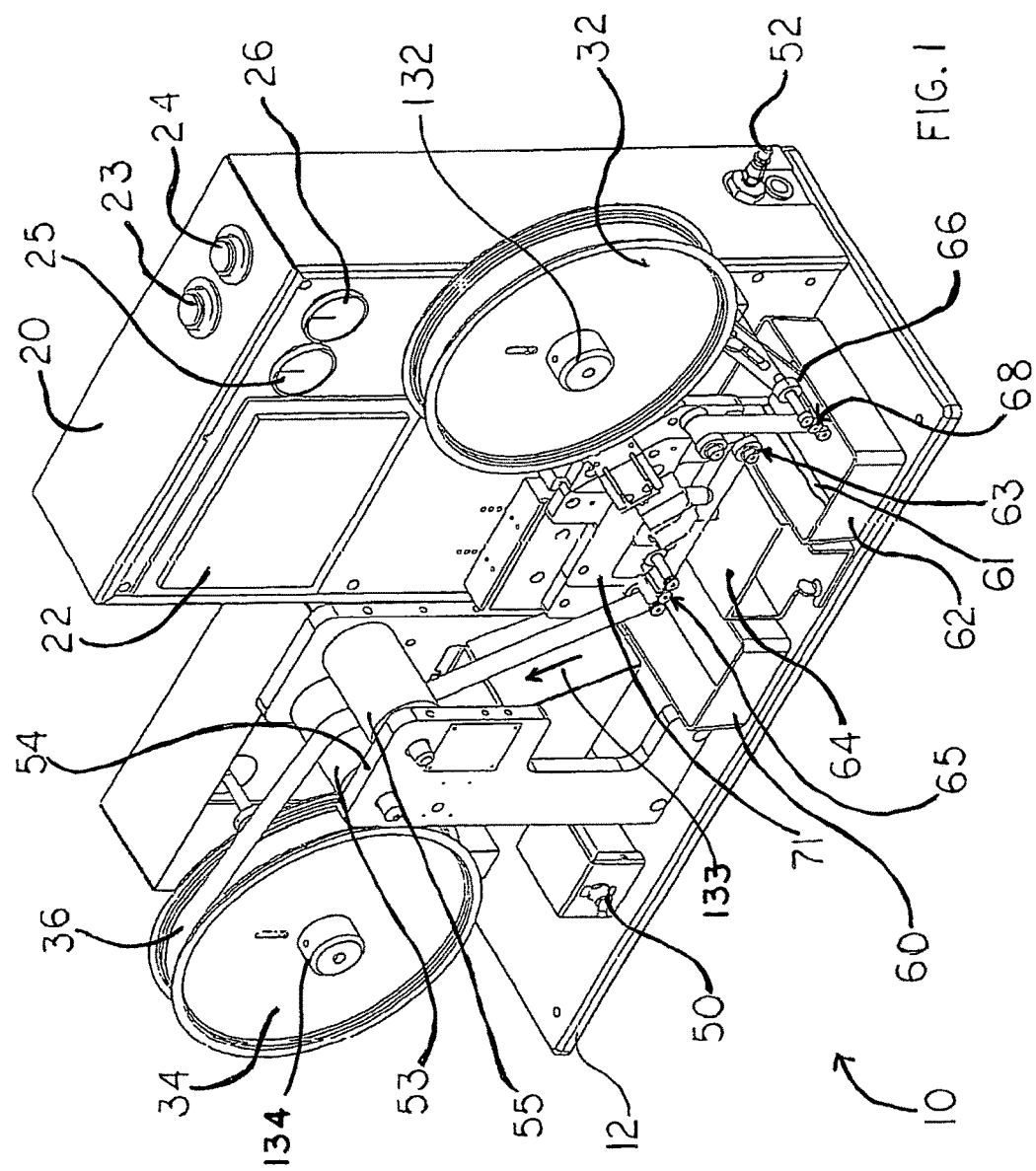
FIG. 1 is a perspective view of the abrasion wear tester showing the abrasive strip threaded.
Figure 2:
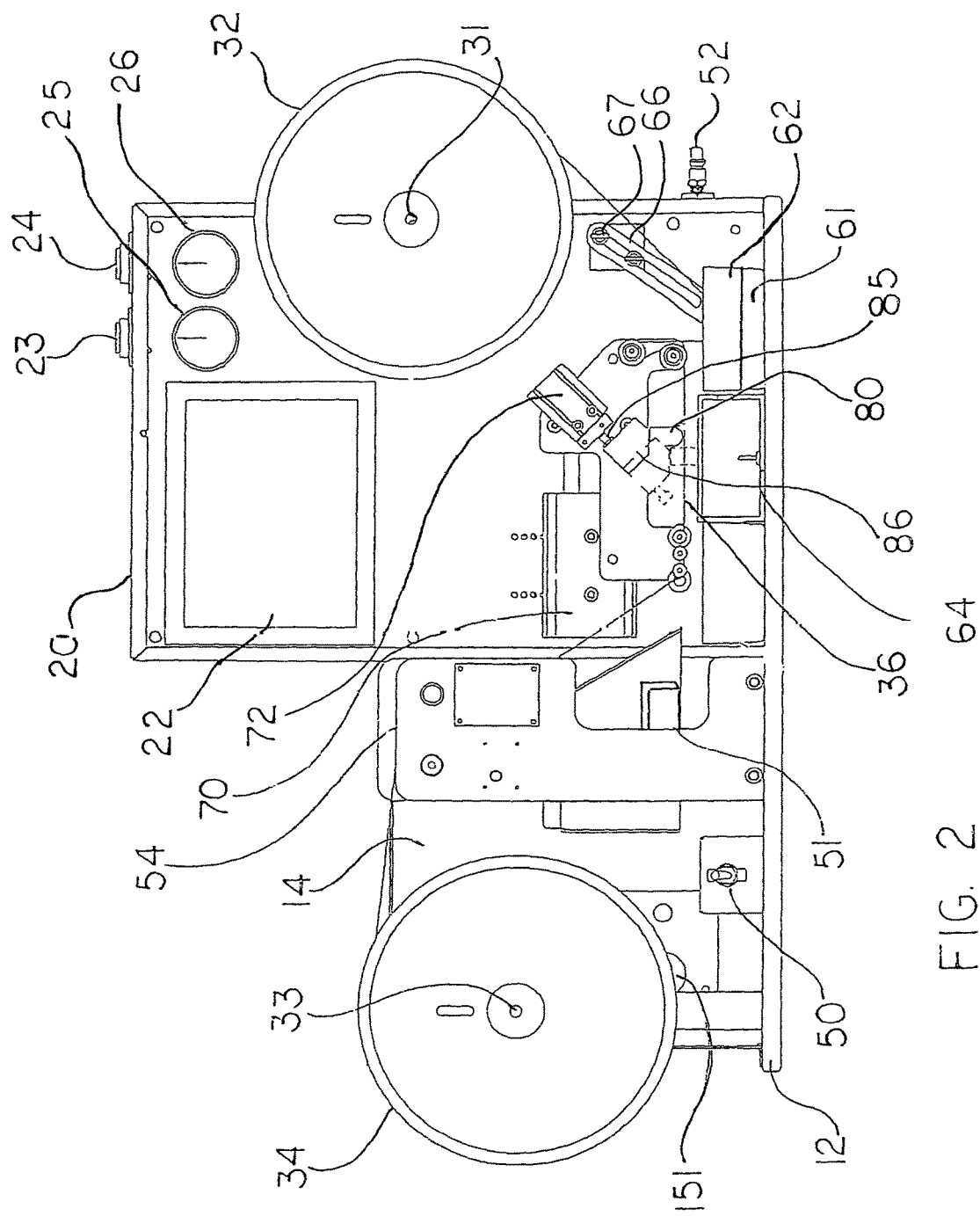
FIG. 2 is front views showing of the abrasion wear tester showing liquid being applied to the abrasion belt together with the following components: main air supply pressure gauge, finger pressure gauge, abrasive paper ribbon feed-off, air supply connection, liquid pan, finger probe assembly, liquid drip pan, abrasive paper, specimen mounting box, main power switch, paper wind-up, drive roller assembly, operators control panel, control box and pressure regulator knobs.

In accordance with the present invention, there is provided an abrasion wear tester 10 as best shown in FIGS. 1-12. Wear tester 10 includes a base plate 12 with a vertical back wall 14 connected perpendicularly to base plate 12. Paper feed-off reel 32 rolls on axle 31 which is rotatably connected to brake means 132 on back wall 14. Paper reel 34 rolls on axle 33 which is rotatably connected to clutch means 134. Clutch means 134 is driven by rewind motor 151. As best shown in FIG. 1, the abrasive strip 36 is a continuous strip of abrasive material being pulled from reel 32 over a series of friction pegs 65 and 68 and guide rollers 63, between drive roller 53 and pressure roller 55 and then rewound back onto reel 34. The abrasive strip or ribbon starts at reel 32 and moves through the friction pegs 68 on peg arm 66, then to guide rollers 63 and friction pegs 65 on ribbon guide assembly 73, then to drive roller 53 and pressure roller 55 on the drive roller assembly 54, and then finally onto reel 34. Braking means is applied to reel 32 to prevent uncontrollable free-wheeling as the ribbon is pulled therethrough. A slight amount of breaking force is applied by brake means 132 to reel 32 to prevent free-wheeling and to help maintain tension in the abrasive ribbon. Brake means 132 is a friction type of brake. In one embodiment, braking is achieved by simply tightening the reel 32 against a non-moving portion of back wall 14.

Figure 6:
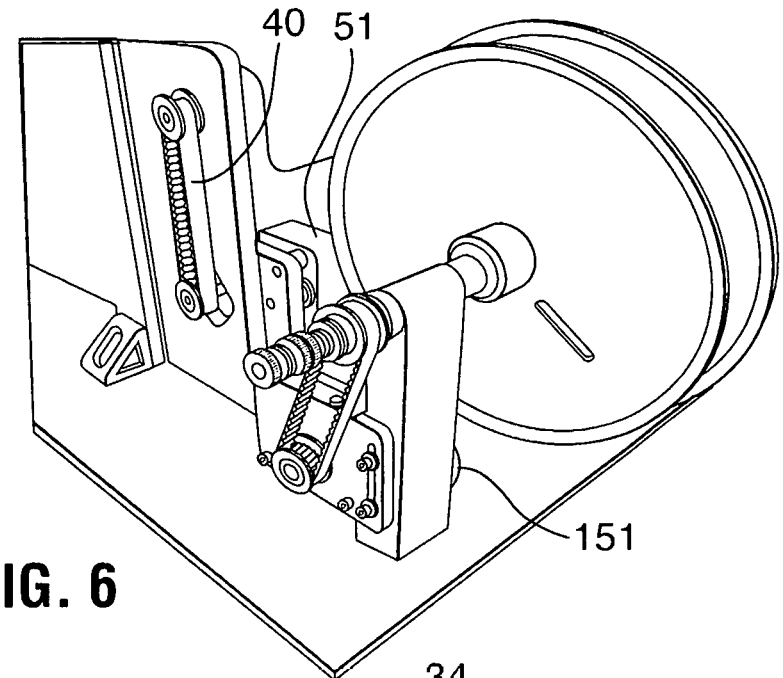
FIG. 6 is a partial rear view of the tester showing the main drive motor, belt and pulleys (14 tooth pulleys), and the rewind or wind-up motor and pulley (15 tooth)

Drive roller 53 is driven by drive motor 51 directly through a belt and pulleys 40, as best shown in FIG. 6. Pressure roller 55 holds ribbon 36 against drive roller 53 to cause drive roller 53 to pull the ribbon. The rewind motor 151 drives reel 34 through a slip clutch 134. It can be seen that, as the ribbon is wound onto reel 34, the diameter of the reel of ribbon will increase. This requires that the relative rotational speed of the drive roller 53 and reel 34 must change as the test progresses. Therefore, reel 34 is driven by rewind motor 151 through a slip clutch means 134 so that, as the reel 34 gets bigger, reel 34 can slow down with respect to drive roller 53, while still rewinding and maintaining tension in the ribbon or abrasive strip.

Figure 7:
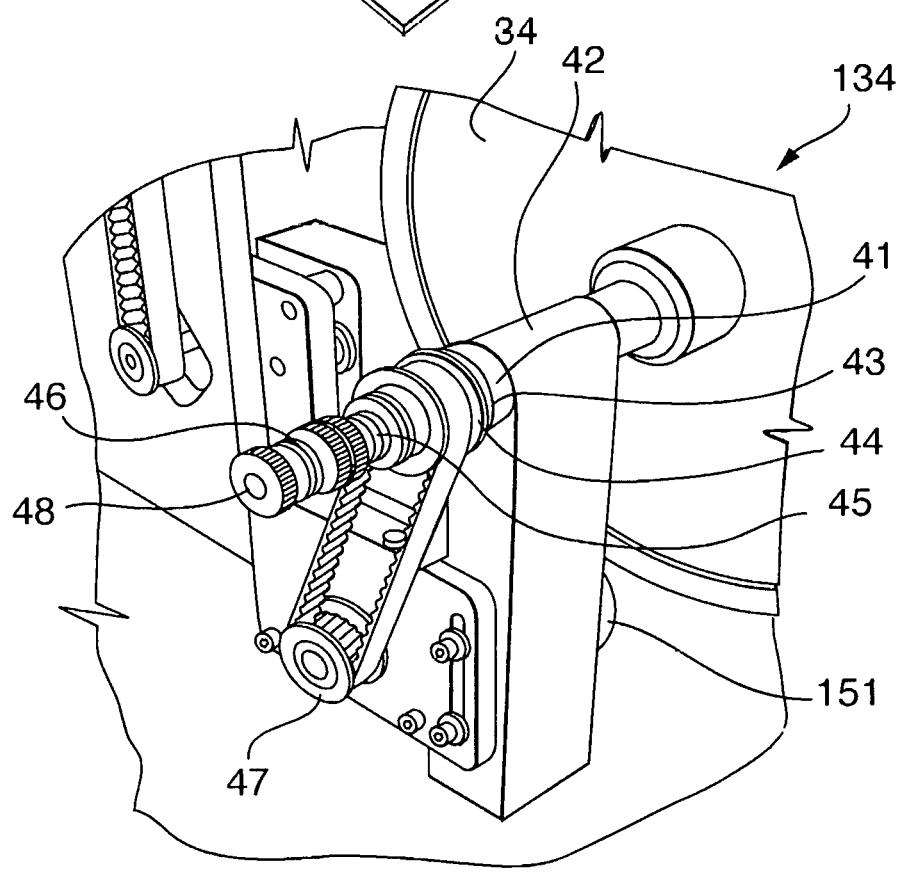
FIG. 7 is a partial rear view of the tester showing the rewind motor, wind-up reel assembly (secured to and rotating with shaft), wind up mount, cutaway view of stationary brass insert, brass collar (secured to and rotates with shaft), leather slip clutch disc (loose and pressed against brass collar via spring), pulley (loose and pressed against clutch disc via spring (14 tooth), brass washer (for wear resistance and steel washer with spring and brass and steel washers), jam nuts, and wind-up motor pulley (15 tooth)

As shown in FIGS. 6 and 7, slip clutch means 134 includes a motor driven pulley and belt 47, a belt driven pulley 44, a leather clutch disc 43, a brass drive collar 41 which is rigidly fixed onto a drive shaft 48 with rewind reel 34 rigidly affixed thereto, a spring 45 and tension adjusting jam nuts 46, and a clutch system mounting bracket 42. As motor 151 drives pulley and belt 47, pulley 44 turns. Pulley 44 is free to turn on drive shaft 48. Pressure from spring 45 causes pulley 44 to bear against leather clutch disc 43 which in turn bears against brass drive collar 41, causing collar 41 to spin. Because collar 41 is fixed onto drive shaft 48, shaft 48 now spins and in turn causes rewind reel 34 to spin. The drive motor 51 drives the drive roller 53 at a selected continuous speed, and therefore, strip 36 is pulled at a continuous speed as well. Because motor 151 also runs at a continuous speed, and because the effective diameter of the ribbon on rewind reel 34 increases as ribbon winds onto reel 34, slippage must occur in the slip clutch 134. This slippage occurs between the drive pulley 44, the leather clutch disc 43 and the brass drive collar 41. The tension in the strip 36 between drive roller 53 and rewind reel 34 is controlled by adjusting the spring 44 tighter or looser by adjusting jam nuts 46.

The ribbon strip guide assembly 73, including a frame 71, two guide rollers 63, three friction pegs or friction studs 65, the finger probe cylinder 72 and finger probe assembly 79, is slidably connected to back wall 14 and slides horizontally in a direction parallel to the movement of the ribbon 36. Pneumatic slide cylinder 70 moves the guide assembly 73 back and forth when activated. The stroke of cylinder 70 is adjustable from 0 to 1 inch. Friction pegs 68 and 65 help to maintain tension in the ribbon 36 as the strip moves through the guide assembly 73, which is especially important when finger probe 80 urges the abrasive strip or ribbon against the test sample 56.

Finger probe 80 includes a replaceable elastomeric tip 82 which is fixed onto a threaded rod 84 and which is then threaded into the piston assembly, including a finger bracket 86 which is in turn rigidly fixed onto the end of the piston 85 in pneumatic cylinder 72. The elastomeric tip 82 is soft and resembles a human finger. During use, tip 82 wears and occasionally needs to be replaced. Finger probe 80 is simply unthreaded from the finger bracket 86, discarded and replaced with a new probe 80.

Figure 9:
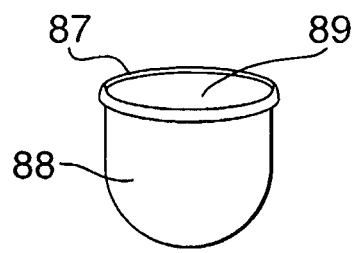
FIG. 9 is a front view of finger probe sleeve.
Figure 10:
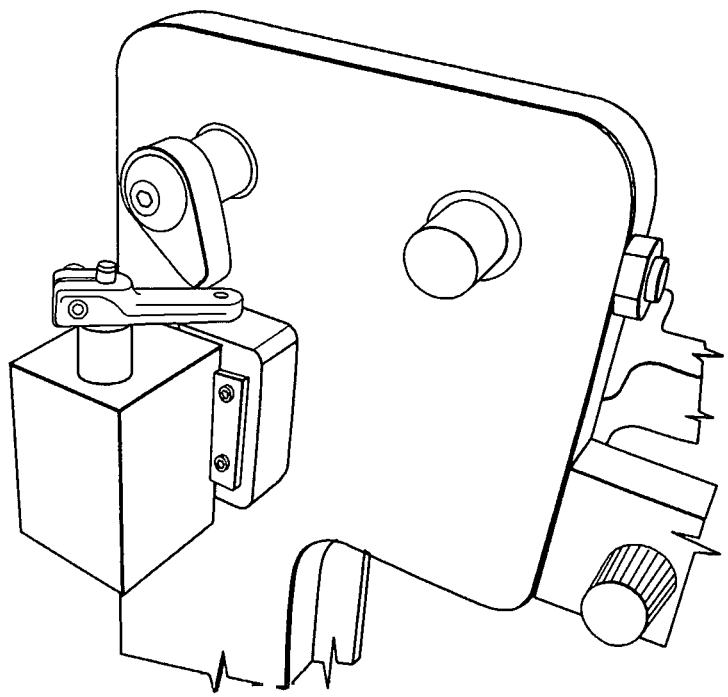
FIG. 10 is a perspective view of Applicant's prior art abrader instrument.
Figure 11:
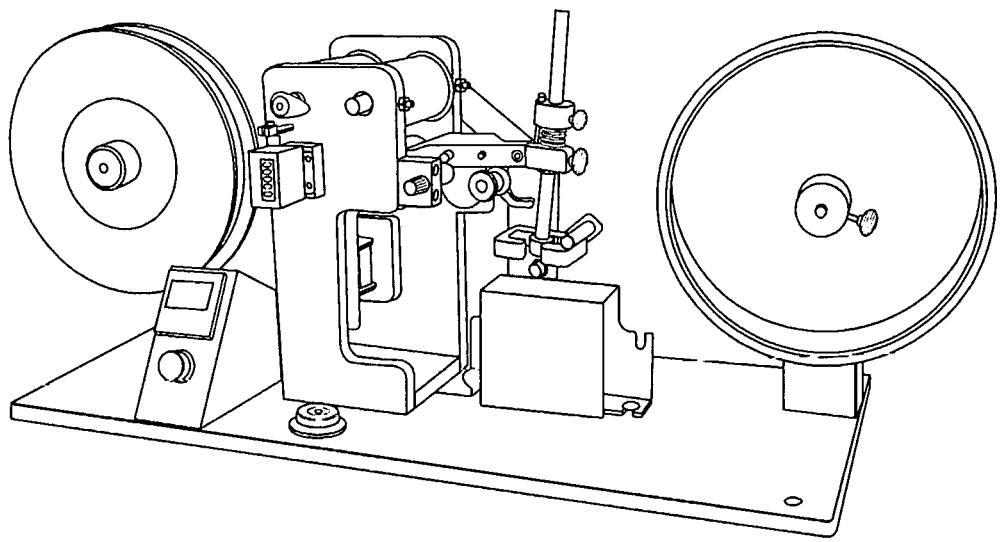
FIG. 11 is a perspective view of Applicants' prior art abrader of FIG. 10, showing date of manufacture of 1986.

Another embodiment contains a harder finger tip 82 which has a replaceable elastomeric sleeve 88, shown in FIG. 9, which is pulled onto finger tip 82 to resemble a human finger. The sleeve 88 stretches and holds tightly to fingertip 82. Sleeve 88 has a thickness 87 and an open end 89 through which is inserted finger tip 82. The combination of finger tip 82 and sleeve 88 have approximately the same shape and hardness as a typical human finger. When the sleeve 88 is worn by a selected amount, or is damaged, sleeve 88 is pulled off and discarded and a new sleeve 88 is slipped onto finger tip 82.

Figure 12:
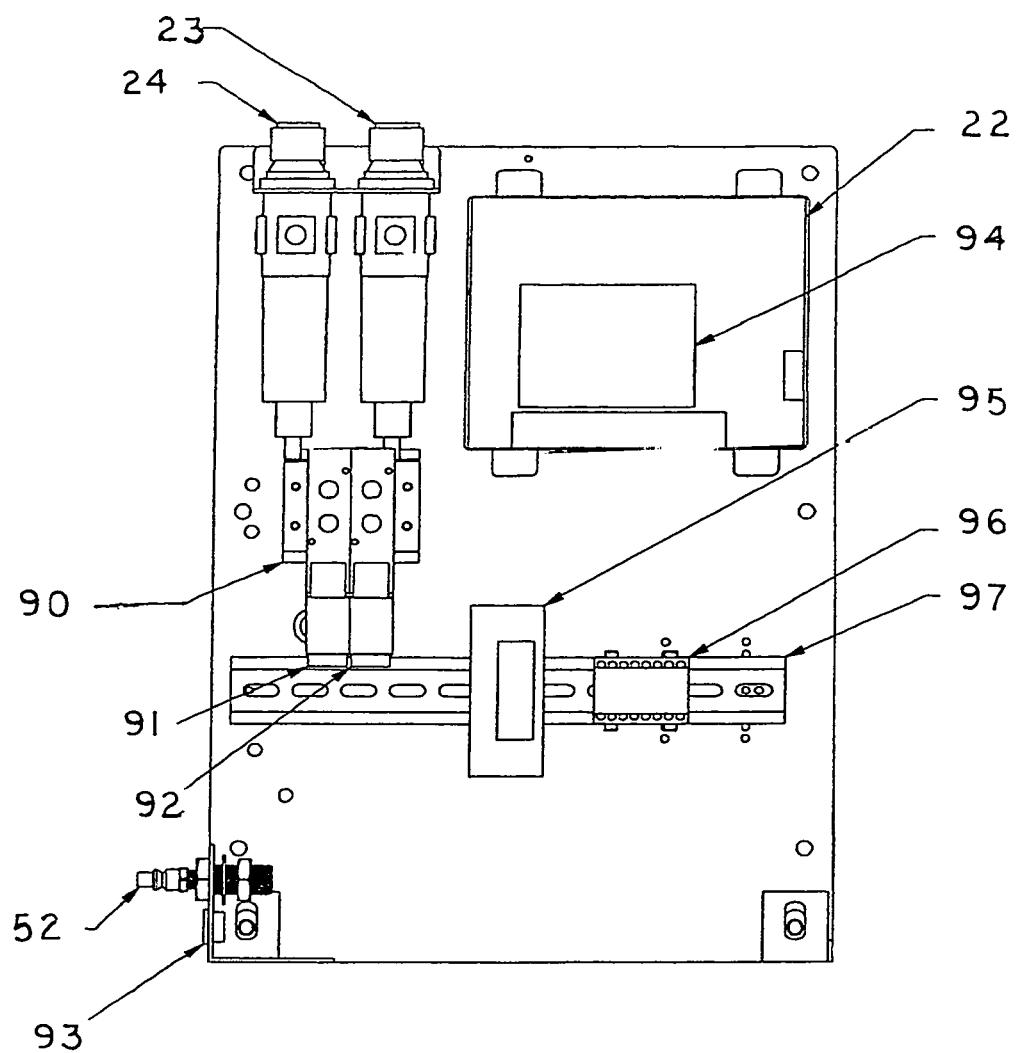
FIG. 12 is a rear view of the abrasion wear tester showing the main system regulator, fine adjustment regulator, power transformer, manifold, and connectors.

FIG. 12 shows a rear view of the abrasion wear tester showing the main system regulator 23, fine adjustment regulator 24, valve manifold 90, valve for finger cylinder 91, valve for slide cylinder 92, quick connect for air supply 52, grommet for power cord 93, rear of operators panel 22, programmable control module 94, 120 VAC or 220 VAC to 24 VDC power transformer 95, terminal block 96, rail 97 for component mounting and mounting angles.

The first air solenoid 170 activates the first pneumatic finger probe cylinder 72 and the second air solenoid 172. activates the second pneumatic slide cylinder 70. Air supply connection 52 provides air to pressure regulator 23, which in turn regulates and supplies air to pressure regulator 24 and to the solenoid 170 which causes the slide cylinder 70 to activate and move the guide assembly back and forth. Main air supply pressure gauge 25 and finger pressure gauge 26 monitor the output of pressure regulators 23 and 24, respectively. Pressure regulator 23 effectively conditions the incoming air so that pressure regulator 24 is not subject to pressure spikes which may be present in the incoming air at connector 52. Pressure regulator 24 controls the amount of pressure to solenoid 172 which activates finger probe cylinder 72 and therefore determines the amount of force which the finger probe 80 applies against the abrasive strip 36 which in turn is pressed against the surface of the test sample 56. Both pressure regulators are adjustable.

Figure 5:
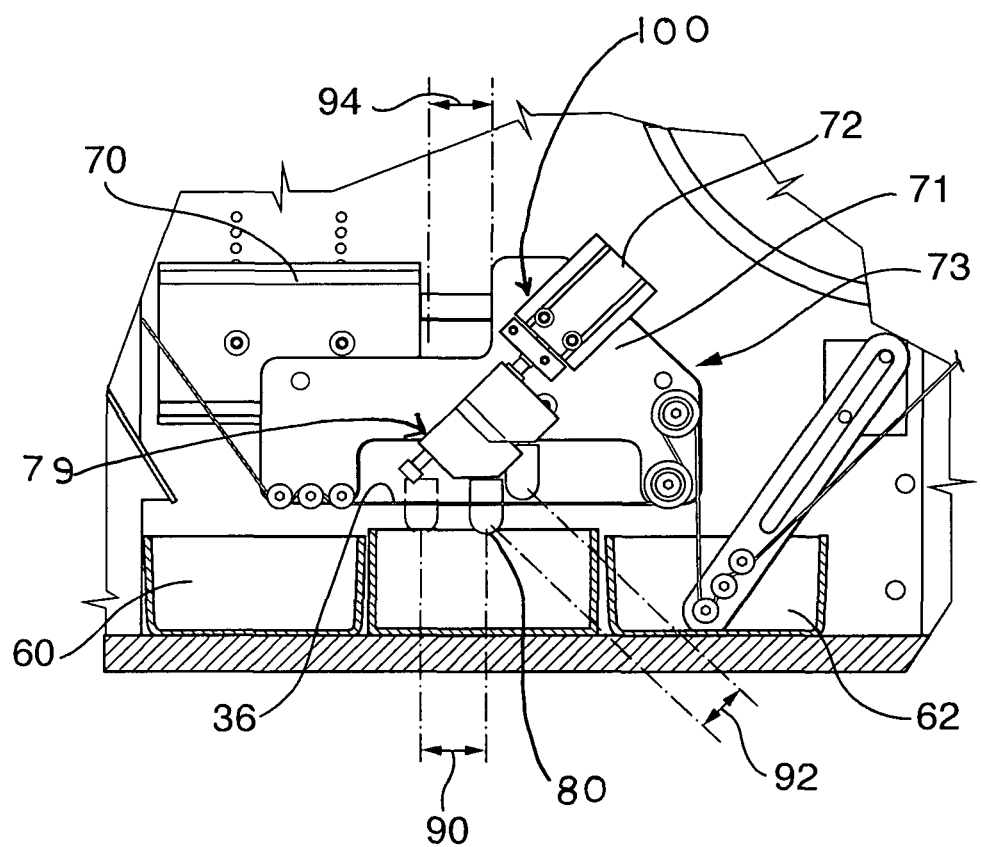
FIG. 5 is partial view of the paper guide area of the abrasion wear tester showing the finger probe cylinder, paper guide assembly, liquid bath, angular travel of finger probe, horizontal travel of paper guide assembly and finger probe, abrasive paper ribbon (travels with finger during finger stroke), liquid drip pan, slide cylinder, and paper ribbon guide assembly movement.

As shown in FIG. 5, the paper guide area of the abrasion wear tester 10 shows the first pneumatic cylinder defining the finger probe cylinder 72, paper guide assembly 100, liquid bath pan 62, angular travel 99 of finger probe 80, horizontal travel 102 of paper guide assembly 100 and finger probe 80 of the second pneumatic cylinder defining the slide cylinder 70 of the paper guide assembly 100 and finger probe 80. The abrasive paper ribbon or strip 36 travels with the finger probe during finger stroke. The length of the stroke for cylinder 70 and therefore, the distance that the guide assembly 73 moves back and forth, is adjustable from 0 inches to 1 inch.

Control box cabinet 20 includes pressure regulators 23 and 24, pressure gauges 25 and 26, operator controller panel 22, controller 21, pneumatic solenoids 170 and 172 and the associated pneumatic tubing and control wiring. A power switch 50 supplies electrical power to the control cabinet.

The test is controlled by electronic controller 21 which activates slide cylinder solenoid 171, finger probe cylinder solenoid 172, rewind motor 151 which drives the paper wind-up or rewind reel 34, and the drive motor 51, which drives drive roller 53 and reel 34.

The operator display panel 22 communicates with and serves as an operator interface with controller 21 and includes a touch sensitive screen which is used to input various control data such as the number of test cycles to be run. Various timers controlling the finger down time, stroke time, and raise and return home time are adjustable on the panel 22. The test start and test pause functions are done at the panel 22, as well. Controller outputs which control the drive motor, rewind motor 151, and the pneumatic solenoids which control finger movement can be activated manually at the panel 22 as desired.

Each test cycle is performed while abrasive strip 36 is being pulled through the tester 10, as follows:

1) The controller 21 energizes solenoid 172 to lower the finger probe against the moving ribbon thus urging the abrasive strip against the test sample;

2) After a selected time delay, controller 21 energizes solenoid 170 to slide the guide assembly 73 to the left and thus the finger 80 and strip 36 across the test sample;

3) After another selected time delay, controller 21 de-energizes both solenoids 170 and 172, thus raising finger probe 80 and strip 36 up away from the test sample 56 and moving the guide assembly 73 back to the starting point, ready for the next cycle.

Figure 3:
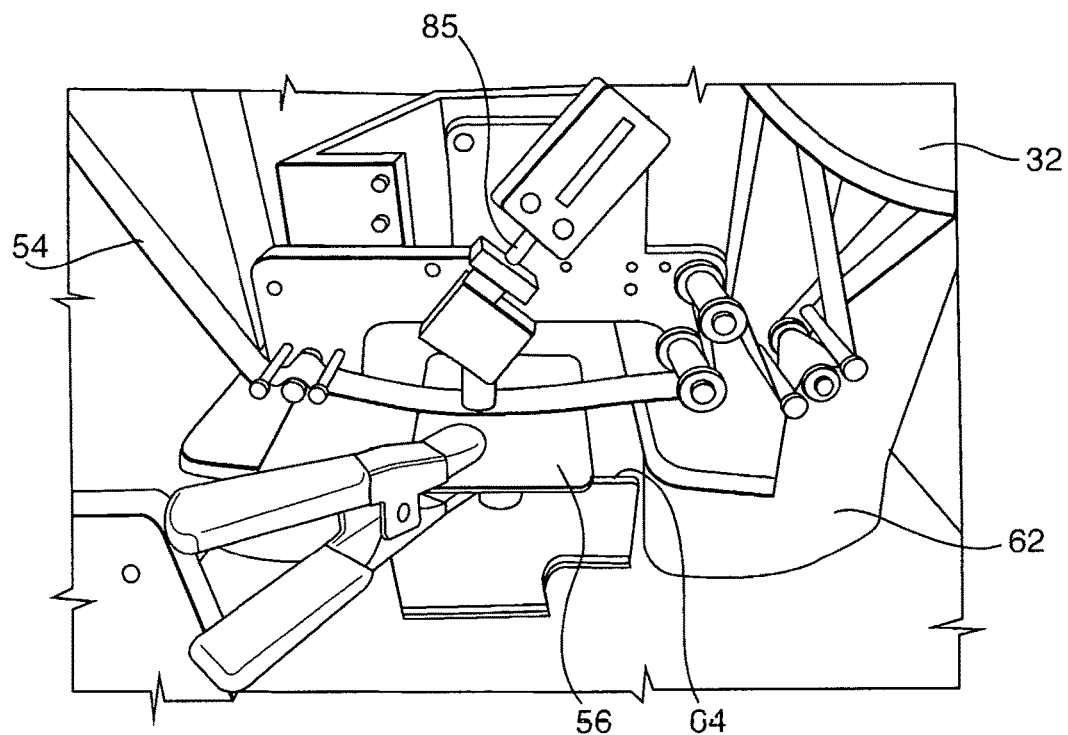
FIG. 3 is a partial front view of a sample being test on the abrasion wear tester.
Figure 4:
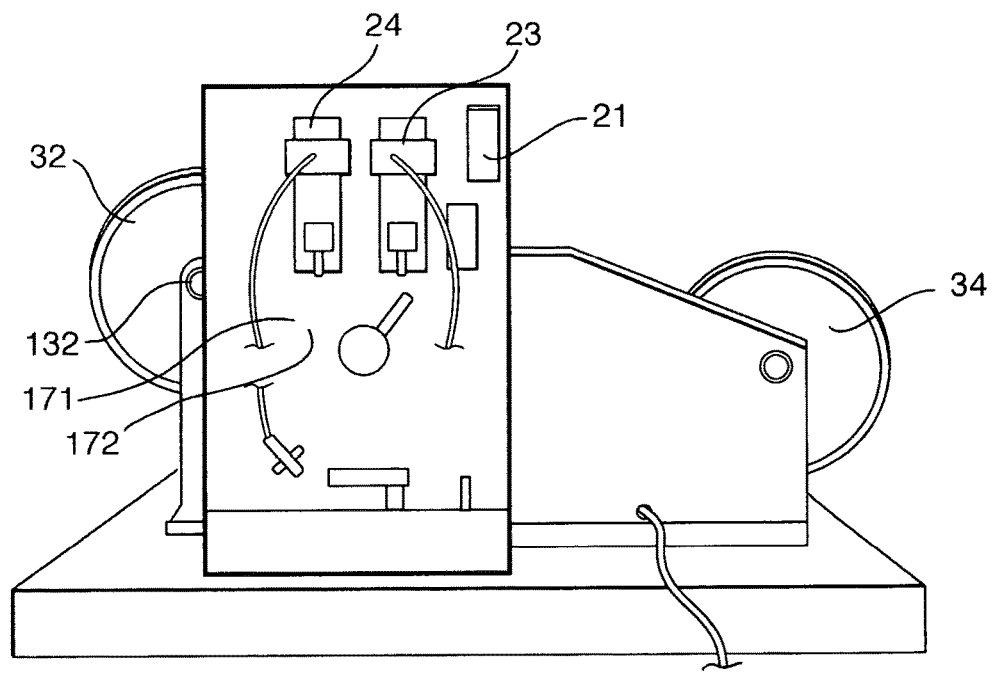
FIG. 4 is a rear view of the abrasion wear tester showing the main system regulator, fine adjustment regulator, valve manifold, valve for finger cylinder, valve for slide cylinder, quick connect for air supply, grommet for power cord, rear of operators panel, programmable control module, 120 VAC or 220 VAC to 24 VDC power transformer, terminal block, rail for component mounting and mounting angles.

A test includes many, perhaps hundreds or thousands of test cycles, as determined by the user. Each test cycle simulates the 'wiping' action which occurs as a finger operates a key. To prepare for the test, the user enters the desired number of cycles to be run, and makes any changes to test cycle timers as is necessary. Then, the user mounts test sample 56, as shown in FIG. 3, to a specimen mounting box 64. When the user activates the test start function, both the drive motor 51 and the rewind motor 151 start and the strip is in motion. The controller 21 now begins cycling as described above and continues until either the selected number of test cycles have been performed or until a test pause function is activated by the user. At the end of a normal test, the user removes the sample and compares the results to other tested samples or to known test standards.

The abrasion tester 10 can be used with or without a liquid being added to the strip 36. A liquid 61, which simulates liquids which may be present on a typical human finger, is contained in liquid bath pan 62. Excess liquid is collected in liquid drip pan 60. Peg arm 66 includes three friction pegs 68 and is slidably connected to tester 10 by two bolts 67. When a particular test requires that a liquid be applied to the strip, the two bolts 67 which hold peg arm 66 are loosened and peg arm 66 is lowered so that the three friction pegs 68 and the strip 36 are in the liquid bath 61, as shown in FIG. 5. Then the two bolts 67 are re-tightened. Liquid is applied to the ribbon or strip as it is pulled through liquid tank or liquid bath pan 62. A special synthetic film, paper, polymer impregnated paper, or plastic film coated paper provides a substrate which will hold an abrasive substance yet not weaken or tear during a test after the liquid is applied is used in this test.

Application

An ASTM (American Society for Testing and Measurement) test has been developed for the use of the abrasion tester of the present invention. A draft of the ASTM test follows:

Examples

The following example further describe the abrasion test of the instant invention, methods of using the instrument, and the tests performed to determine the various characteristics of the material compositions subjected to wear. The examples are provided for exemplary purposes to facilitate understanding of the invention and should not be construed to limit the invention to the examples.

Standard Test Method for Determining the Abrasion Resistance of Inks and Coatings on Membrane Switches Using the Norman Tool Abrader—Wet Method This test method describes the procedure for subjecting inks or coatings on membrane switches to an abrasive medium at a specified force while exposed to a specified fluid. Within certain limitations, the test method is applicable for materials including, but not limited to: printed or coated polyester, polycarbonate, and silicone rubber. The samples can be either flat or contoured. The terminology for membrane switches is set forth in ASTM IEC 60068-2-70, "Abrasion of markings and letterings caused by rubbing of fingers and hands".

The term final breakthrough defines the number of cycles until complete removal of the first surface ink or coating being tested. The term membrane switch defines a momentary switching device in which at least one contact is on, or made of a flexible substrate. The term wear limit defines in testing membrane switches, the number of cycles until an underlying layer of different color may be seen through the first layer.

Membrane Switch keys are subjected to repeated actuations, usually by a human finger. They are also subjected to other conditions (for example, wiping, cleaning, rubbing) during handling, end-use, shipment, or storage that may cause abrasion damage. The result may be a significant removal of the coatings, text or decorative inks. This test method is applicable to a wide range of materials. The main criterion is that the abrasion process produces visible wear or breakthrough in the surface being tested. The amount of abrasion damage to a surface is dependent on numerous variables. This test method provides a way of comparing relative abrasion resistance of inks and coatings. In no way do the results provide a correlation value of the number of human finger touches before coating failure. It only provides a means to compare results of tests performed using the same equipment, abrasive materials and loading conditions. The test method can be used for quality control purposes, as a research and development tool, to evaluate material combinations for a given application, or for the comparison of materials with relatively similar properties.

Interferences include inconsistent wear can occur which will compromise the results. Caution is necessary to ensure the mounting method does not deflect the specimen, which may influence the wear characteristics. Contoured surfaces can be tested but results may be more difficult to duplicate and some equipment is not designed to test non-flat surfaces. Whenever possible, a smooth surface is preferred. Extra care should be taken when evaluating a non-uniform surface (that is, rough surface), and for the user to recognize potential variations between specimens.

The present invention is capable of providing cyclic exposure of a test specimen to an abrasion system, which consists of an abrasive medium and a fluid component, under controlled loading conditions. The specimen mounting fixture or holder is a suitable device of sufficient strength and rigidity used to secure the specimen so that it is held rigidly to the load during testing. One preferred abrasive media comprises a ribbon of material having a width of 17.3 mm (0.68 inch) available from NORMAN TOOL.

Abrasive media and specimen conditioning conditions the specimens for at least 24 h at 25+/−10° C. and 50+/−10% relative humidity. The test are conducted in the standard laboratory atmosphere of 25+/−10° C. and 50+/−10% relative humidity.

The pre-test setup consists of mounting the test specimen on the mounting fixture. This holding device should firmly hold the test specimen in a fixed position, without distortion, such that the force probe makes contact to the specimen target area. Specimens shall be cleaned in such a way that the surface is free from grit, grease, fingerprints or other contaminates. Use a clean lint-free piece of absorbent material and either reagent grades of n-heptane or isopropyl alcohol. Inspect for residue and quality of ink or coating in area of test. Next setup specified abrasive system, adjust the test force on probe to specified value. Align the specimen targeted test point to the applied force probe, adjust force on probe as specified and start the abrasion process.

Subject the test specimen to abrasion for the specified number of cycles; or until sought after visual change has been detected. Wear Limit is determined when an underlying layer of different color may be seen through the first layer. In determining the extent of wear, interrupt the instrument every 5 cycles for examination of the test specimen. Final breakthrough, not wear, on a first surface printed line constitutes a failure regardless of size. When the test is stopped prior to achieving final end point, it is recommended the specimen not be moved. Doing so may present problems in aligning the wear path for additional testing.

The report should include the following information:
10.1.1 Model number and description of Abrasion Tester used,
10.1.2 Abrasive material,
10.1.3 Test Fluid,
10.1.4 Force applied to specimen,
10.1.5 Number of cycles to wear limit,
10.1.6 Number of cycles to final breakthrough, 10.1.7 Temperature and humidity, 10.1.8 Identity of specimen, describing the material or coating, 10.1.9 Method of cleaning, if applicable, and 10.1.10 Visual evaluation of test specimen and include photos of target test area, if possible.

ASTM test F1597 has been established which includes the use of a finger probe which is exemplary of that of the present invention.

The test is designated as Designation: F 1597-01 and is entitled: "Standard Test Method for Determining the Actuation Force and Contact Force of a Membrane Switch".

This standard is issued under the fixed designation F 1597. The number immediately following the designation indicates the year of original adoption or, in the case of revision, the year of last revision. A number in parentheses indicates the year of last reapproval. A superscript epsilon indicates an editorial change since the last revision or reapproval.

This test method covers the measurement of actuation force or contact force, or both, of a membrane switch utilizing a pre-determined resistance value. Referenced documents include ASTM Standards: D 2240 Test Method for Rubber Property Durometer Hardness and F 1570 Test Method for Determining the Tactile Ratio of a Membrane Switch which is a momentary switching device in which at least one contact is on, or made of a flexible substrate.

Method of Use

Specified resistance is the maximum allowable resistance as measured between two terminations whose internal switch contacts are held closed to complete a circuit. It is useful to manufacturers and users when designing membrane switch interface circuitry.

Actuation force is the maximum force measure prior to or including point at which contact closure is achieved on a membrane switch. Contact force is the force at contact closure are useful to manufacturers and users in determining the suitability, preference and aesthetics of a membrane switch in a given application.

The apparatus includes a test probe fully specified and recorded which is to be used throughout the duration of the test. A Tactile switch is utilized comprising a switch assembly that provides a tactile ratio greater than zero and must be n Non-elastic. A non-tactile switch used comprises a switch assembly that has a tactile ratio equal to zero which comprises an inert elastomeric material having a material hardness=A/456 5 per Test Method D 2240.

Figure 8:
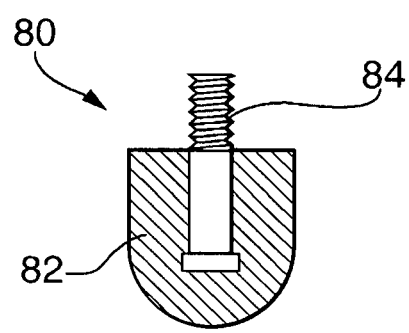
FIG. 8 is a front view of finger probe.

The size and shape of the probe is shown in FIGS. 8 and 9. The test surface comprises a flat, smooth, unyielding and larger than switch under test. The instrument must be capable of holding the test probe securely and provide perpendicular movement into and away from switch under test. A resistance measuring device, for example, an Ohm meter should be utilized so that it does not apply a voltage outside the operating range of the switch contacts. The instant wet abrasion instrument provides a suitable monitoring device to measure force on test probe.

The procedure requires a pre-test setup including the steps of securing the switch on the test surface, preconditioning the switch by depressing manually 25 times, positioning the test probe over the desired area of switch, lowering the probe until the tip is just above top surface of switch without touching, and connecting the switch terminals to resistance measuring device.

The in process test comprises the steps of activating the test probe movement down at a rate not to exceed 13 mm/s and monitoring the force and resistance during probe movement. Upon achieving the specified resistance defined as contact closure, the force on the probe is recorded as contact force. At that point, downward movement of test probe is stopped and the maximum force on the probe seen during probe movement as actuation force is recorded. The value can be greater than or equal to the contact force. The test probe is retracted until the lower probe tip is just about the top surface of the switch, but not touching. The procedure is repeated four more times. The averages of five readings are determined and recorded as contact force and actuation force.

The data obtained should include the temperature, humidity, barometric Pressure, test probe shape and durometer, actuation force, contact force, specified resistance, description of probe holding fixture and monitoring device, part number or description of switch, or both, and the date of test.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplification presented herein above. Rather, what is intended to be covered is within the spirit and scope of the appended claims.

I claim:

1. An abrasive tester for testing the wear resistance of the surface of a selected test sample comprising:

a base member;

a frame extending from and supported by said base member;

an abrasive strip contained on a rotatable supply reel having a brake means;

said abrasive strip is selected from the group consisting of a paper strip, a synthetic strip, and a combination paper and synthetic strip each one including an abrasive surface;

a peg arm slidably connecting to said frame, said peg arm including at least one friction stud connecting to said peg arm for providing tension to said abrasive strip as said strip is pulled through over said at least one friction stud;

a guide assembly including at least one guide roller slidably connected to said frame;

a finger probe connecting to a piston assembly extending from a first pneumatic finger probe cylinder mounting to said guide assembly, said finger probe extendable against said abrasive strip urging said abrasive strip against a test sample;

a second pneumatic slide cylinder moving said guide assembly to and from a start position;

a first air solenoid in fluid communication with said first pneumatic finger probe cylinder;

a second air solenoid in fluid communication with said second pneumatic slide cylinder;

a first air pressure regulator supplying air at a regulated pressure to said first air solenoid at a selected pressure which is appropriate to urge said finger probe against said strip and said test sample at a selected force;

a second air pressure regulator capable of supplying air at a regulated pressure to said second air solenoid at a selected pressure required to slide said guide assembly to and from said start position;

a drive roller assembly including a drive roller and a pressure roller rotatably in cooperative engagement with a drive motor pulling said abrasive strip against said finger probe;

a rewind reel capable of rewinding said abrasive strip feeding from said drive roller;

a controller controlling said first air solenoid and said second air solenoid, said roller drive motor and said rewind motor, said controller programmable for a selected number of tests comprising multiple test cycles, said controller capable of providing automatic control of said drive motor, said rewind motor and said first air solenoid and said second air solenoid controlling movement of said abrasive strip against said test sample; and an operator display panel capable of providing communication between an operator and said controller.

2. The abrasive tester of claim 1 wherein said controller providing selective control of said drive motor, said rewind motor and said first air solenoid and said second air solenoid.

3. The abrasive tester of claim 1 wherein said abrasive strip is pre-treated with a selected liquid and abrading of a given test sample using said abrasive tester.

\* \* \* \* \*